US009008373B2

(12) United States Patent
Markovsky et al.

(10) Patent No.: US 9,008,373 B2
(45) Date of Patent: *Apr. 14, 2015

(54) DEVICE, SYSTEM AND METHOD FOR TRANSIT TESTING OF SAMPLES

(75) Inventors: Robert J. Markovsky, Brentwood, NH (US); Stanley E. Charm, Boston, MA (US); Richard T. Skiffington, North Reading, MA (US)

(73) Assignee: Charm Sciences, Inc., Lawrence, MA (US)

( * ) Notice: Subject to any disclaimer, the term of this patent is extended or adjusted under 35 U.S.C. 154(b) by 301 days.

This patent is subject to a terminal disclaimer.

(21) Appl. No.: 13/696,445

(22) PCT Filed: May 6, 2011

(86) PCT No.: PCT/US2011/035576
§ 371 (c)(1),
(2), (4) Date: Mar. 26, 2013

(87) PCT Pub. No.: WO2011/140476
PCT Pub. Date: Nov. 10, 2011

(65) Prior Publication Data
US 2013/0177214 A1    Jul. 11, 2013

Related U.S. Application Data

(60) Provisional application No. 61/331,854, filed on May 6, 2010, provisional application No. 61/377,287, filed on Aug. 26, 2010, provisional application No. 61/454,771, filed on Mar. 21, 2011.

(51) Int. Cl.
*G01N 33/04* (2006.01)

(52) U.S. Cl.
CPC ..................................... *G01N 33/04* (2013.01)

(58) Field of Classification Search
None
See application file for complete search history.

(56) References Cited

U.S. PATENT DOCUMENTS

| | | | | |
|---|---|---|---|---|
| 4,188,246 A | * | 2/1980 | Lipshaw | 156/57 |
| 4,264,560 A | * | 4/1981 | Natelson | 422/417 |
| 4,540,659 A | | 9/1985 | Litman et al. | 435/7 |
| 4,700,714 A | | 10/1987 | Fuisz | 128/767 |
| 4,703,017 A | | 10/1987 | Campbell et al. | 436/501 |
| 4,743,560 A | | 5/1988 | Campbell et al. | 436/501 |
| 4,826,759 A | | 5/1989 | Guire et al. | 435/4 |
| 4,999,285 A | | 3/1991 | Stiso | 438/7.9 |

(Continued)

FOREIGN PATENT DOCUMENTS

| | | | | |
|---|---|---|---|---|
| EP | 0 321 145 | 12/1987 | | G01N 33/543 |
| EP | 0 279 574 | 2/1988 | | G01N 33/52 |

(Continued)

OTHER PUBLICATIONS

"A Short Guide—Developing Immunochromotagraphic Test Strips," 1996, pp. 1-36.

(Continued)

*Primary Examiner* — Jayesh A Patel
*Assistant Examiner* — Mai Tran
(74) *Attorney, Agent, or Firm* — MacCord Mason PLLC

(57) ABSTRACT

Disclosed herein is a method and device for testing an agricultural product for the presence of an unwanted residue including a reader-incubator combination that can utilize onboard motor vehicle systems, such as an onboard microprocessor and onboard power supply.

20 Claims, 12 Drawing Sheets

(56) References Cited

U.S. PATENT DOCUMENTS

| | | | |
|---|---|---|---|
| 5,158,869 A | 10/1992 | Pouletty et al. | 435/7.9 |
| 5,179,005 A | 1/1993 | Phillips et al. | 435/14 |
| 5,208,535 A | 5/1993 | Nakayama et al. | 324/318 |
| 5,229,073 A | 7/1993 | Luo et al. | 422/56 |
| 5,238,652 A | 8/1993 | Sun et al. | 422/61 |
| 5,260,222 A | 11/1993 | Patel et al. | 436/180 |
| 5,266,497 A | 11/1993 | Imai et al. | 436/514 |
| 5,296,347 A | 3/1994 | LaMotte, III | 435/5 |
| 5,356,782 A | 10/1994 | Moorman et al. | 435/7.9 |
| 5,395,754 A | 3/1995 | Lambotte et al. | 435/607.4 |
| 5,434,053 A | 7/1995 | Piasio | 435/79 |
| 5,451,504 A | 9/1995 | Fitzpatrick et al. | 435/7.2 |
| 5,521,102 A | 5/1996 | Boehringer et al. | 436/523 |
| 5,541,059 A | 7/1996 | Chu | 435/5 |
| 5,541,069 A | 7/1996 | Mortensen et al. | 435/7.9 |
| 5,545,721 A | 8/1996 | Carroll et al. | 530/391.7 |
| 5,585,241 A | 12/1996 | Lindmo | 435/6 |
| 5,591,645 A | 1/1997 | Rosenstein | 436/514 |
| 5,602,040 A | 2/1997 | May et al. | 436/514 |
| 5,622,871 A | 4/1997 | May et al. | 436/514 |
| 5,656,448 A | 8/1997 | Kang et al. | 435/7.94 |
| 5,656,502 A | 8/1997 | MacKay et al. | 436/180 |
| 5,698,390 A | 12/1997 | Houghton et al. | 435/5 |
| 5,712,172 A | 1/1998 | Huang et al. | 436/518 |
| 5,714,389 A | 2/1998 | Charlton et al. | 436/514 |
| 5,726,010 A | 3/1998 | Clark | 435/5 |
| 5,726,013 A | 3/1998 | Clark | 435/5 |
| 5,739,041 A | 4/1998 | Nazareth et al. | 436/518 |
| 5,753,517 A | 5/1998 | Brooks et al. | 436/514 |
| 5,766,962 A | 6/1998 | Childs et al. | 436/518 |
| 5,780,308 A | 7/1998 | Ching et al. | 436/514 |
| 5,939,272 A | 8/1999 | Buechler et al. | 435/7.1 |
| 5,962,339 A | 10/1999 | Midgely | 436/534 |
| 5,985,675 A | 11/1999 | Charm et al. | 436/514 |
| 6,001,658 A | 12/1999 | Fredrickson | 436/514 |
| 6,121,008 A | 9/2000 | Fitzpatrick et al. | 435/5 |
| 6,177,281 B1 | 1/2001 | Manita | 436/518 |
| 6,258,323 B1 | 7/2001 | Hormann et al. | 422/99 |
| 6,281,004 B1 | 8/2001 | Bogen et al. | 435/287.1 |
| 6,319,466 B1 | 11/2001 | Markovsky et al. | 422/56 |
| 6,368,876 B1 | 4/2002 | Huang et al. | 436/518 |
| 6,475,805 B1 | 11/2002 | Charm et al. | 436/514 |
| 6,509,196 B1 | 1/2003 | Brooks et al. | 436/514 |
| 6,656,744 B2 | 12/2003 | Pronovost et al. | 436/514 |
| 6,663,833 B1 | 12/2003 | Stave et al. | 422/81 |
| 6,699,722 B2 | 3/2004 | Bauer et al. | 436/518 |
| 7,410,808 B1 | 8/2008 | Saul et al. | 436/514 |
| 7,863,057 B2 | 1/2011 | Saul et al. | 436/518 |
| 8,005,280 B2 * | 8/2011 | Mott et al. | 382/128 |
| 2003/0049857 A1 | 3/2003 | Chan | 436/170 |
| 2003/0162236 A1 | 8/2003 | Harris et al. | 435/7.92 |
| 2003/0190368 A1 | 10/2003 | Stoughton et al. | 424/556 |
| 2003/0199004 A1 | 10/2003 | Fong | 435/7.9 |
| 2004/0002063 A1 | 1/2004 | Chan et al. | 435/5 |
| 2004/0002165 A1 | 1/2004 | Buchannan et al. | 436/180 |
| 2004/0161859 A1 | 8/2004 | Guo et al. | 436/514 |
| 2004/0171092 A1 | 9/2004 | Harris et al. | 435/7.92 |
| 2004/0241750 A1 | 12/2004 | Nordman et al. | 435/7.1 |
| 2004/0241882 A1 | 12/2004 | DiNello et al. | 436/518 |
| 2006/0115896 A1 | 6/2006 | Wong et al. | 435/345 |
| 2006/0286627 A1 | 12/2006 | Bochner et al. | 435/40.5 |
| 2010/0129789 A1 | 5/2010 | Self et al. | 435/5 |
| 2011/0255756 A1 | 10/2011 | Harris et al. | 382/128 |
| 2012/0064637 A1 | 3/2012 | Dinello et al. | 436/501 |
| 2014/0057362 A1 * | 2/2014 | Markovsky et al. | 436/171 |

FOREIGN PATENT DOCUMENTS

| | | | |
|---|---|---|---|
| EP | 0 291 176 | 4/1988 | G01N 33/558 |
| EP | 0 291 194 | 4/1988 | G01N 33/543 |
| EP | 0 299 428 | 7/1988 | G01N 33/543 |
| EP | 0 306 336 | 9/1988 | G01N 33/543 |
| EP | WO 90/15327 | 12/1990 | G01N 33/543 |
| EP | 0 516 095 | 5/1992 | G01N 33/53 |
| EP | 0 544 413 | 10/1992 | C12Q 1/18 |
| EP | 0 582 231 | 7/1993 | G01N 33/558 |
| EP | 0 284 232 | 6/1995 | G01N 33/558 |
| EP | 0 378 391 | 9/1995 | G01N 33/50 |
| EP | 0 593 112 | 8/1998 | G01N 33/94 |
| GB | 2477799 A * | 8/2011 | B60P 3/14 |
| WO | WO 91/19980 | 12/1991 | G01N 33/558 |
| WO | WO 92/22797 | 12/1992 | |
| WO | WO 93/03175 | 2/1993 | C12Q 1/00 |
| WO | WO 94/02850 | 2/1994 | G01N 33/53 |
| WO | WO 94/23300 | 10/1994 | G01N 33/558 |
| WO | WO 96/38720 | 12/1996 | G01N 21/00 |
| WO | WO 96/42017 | 12/1996 | G01N 33/543 |
| WO | WO 97/03209 | 1/1997 | C12Q 1/66 |
| WO | WO 97/05287 | 2/1997 | C12Q 1/68 |
| WO | WO 02/10708 | 2/2002 | |
| WO | WO2004/109285 | 12/2004 | G01N 33/558 |
| WO | WO 2011/140476 | 11/2011 | |

OTHER PUBLICATIONS

Verheijen, et al., "Single-Step Strip Tests for Residue Analyses," DLO—State Institute for Quality Control of Agricultural Products (RIKILT-DLO) Jun. 3, 1998).
Wong, "Chemistry of Protein Conjugation and Cross-Linking," 39-40; 122-123; 195-204 copyright 1991.
Charm, et al., "Microbial Receptor Assay for Rapid Detection and Identification of Seven Families of Antimicrobial Drugs in Milk," Collaborative, Study; J. Assoc. Off. Anal. Chem., 304-316, vol. 71, No. 2.
Brady, et al., "Resistance Development Potential of Antibiotic/Antimicrobial Residue Levels Designated as 'Safe Levels'," J. of Food Protection, 56(3):229-233, Mar. 1993.
Charm, et al., "An Integrated System Monitoring Milk for FDA 'Safe Levels' Using Charm Test Methods," J. Assn. of Food & Drug Officials, 58(1), 17-29, Jan. 1994.
Hassnoot, et al.,"Evaluation of a Sol Particle Immunoassay (SPIA) Based Single-Step Strip Test for the Detection of Sulfadimidine Residues," Euroresidue III (1996) pp. 461-465.
Hermanson,"Bioconjugate Techniques," Academic Press, 1996, pp. 169-186.
Hermanson et al.,"Immobilized Affinity Ligand Techniques," pp. 98-110, 1992, Academic Press copyright 1992.
Wong,"Chemistry of Protein Conjugation and Cross-Linking," pp. 122-123, Boca Raton, Fla.
Wong,"Chemistry of Protein Conjugation and Cross-linking," pp. 195-204, 1991, Boca Raton Florida.
Hermanson,"Bioconjugate Techniques," pp. 169-186, 1996, San Diego, Calif.
Wong, "Chemistry of Protein Conjugation and Cross-Linking," pp. 122-123, Boca Raton, Fla.
Wong, "Chemistry of Protein Conjugation and Cross-linking," pp. 195-204, 1991, Boca Raton Florida.
Hermanson, "Bioconjugate Techniques," pp. 169-186, 1996, San Diego, Calif.

* cited by examiner

DEVICE, SYSTEM AND METHOD FOR TRANSIT TESTING OF SAMPLES

REFERENCE TO PRIOR APPLICATION

This application is based on and claims priority from U.S. Provisional Patent Application Nos. 61/331,854, filed May 6, 2010; 61/377,287, filed Aug. 26, 2010; and 61/454,771, filed Mar. 21, 2011, the teachings of which are incorporated herein by this reference.

FIELD

This disclosure relates generally to a device and method for diagnostic test incubation and analysis and, more particularly, diagnostic test incubation analysis utilizing systems onboard a motor vehicle.

BACKGROUND

Milk tankers often collect milk from a variety of sources. Such milk can be delivered to a central processing or storage facility. Typically, diagnostic tests are run on the milk at the central facility. For example, the milk can be tested and analyzed for a variety of antibiotics and toxins. In some cases, however, it is useful for the central facility to have test results before the milk arrives. Advance notice can also allow the central facility to divert contaminated, or otherwise less desirable, milk for other purposes or not receive contaminated milk at all. It is desirable to avoid a long drive with contaminated milk that is unacceptable to the central facility. It is also desirable to avoid a delay in unloading good milk, while awaiting a test result.

A central facility might want milk from each source, for example each farmer, to be tested prior to loading onto a milk tanker. If a tanker is contaminated then the central facility will want a separate record of where the contamination originated. In addition, such a record will prevent dilution of bad milk with good milk from shielding the source of the contamination from consequences even if that tanker later becomes diluted so that the contamination is below "acceptable" levels. It is also desirable to test milk prior to loading onto a tanker and, thereby prevent commingling of contaminated milk with uncontaminated milk.

Lateral-flow or immunochromatographic test kits and methods for the detection of the presence or concentration of chemical analytes and residues, such as antibiotics, in liquid samples, some with sensitivity adjustment, are known in the art. Such tests include those described in U.S. Pat. No. 7,410,808, issued Aug. 12, 2008; U.S. Pat. No. 7,097,983, issued Aug. 29, 2006; U.S. Pat. No. 6,475,805, issued Nov. 5, 2002; U.S. Pat. No. 6,319,466, issued Nov. 20, 2001; U.S. Pat. No. 5,985,675, issued Nov. 16, 1999 and U.S. patent application Ser. No. 11/883,784, filed Aug. 6, 2007, all of which are hereby incorporated herein by this reference. Such tests are among those that can be used to cost-effectively test milk, and other agricultural products while in transit thereby improving transport logistics.

SUMMARY

Figure 1:
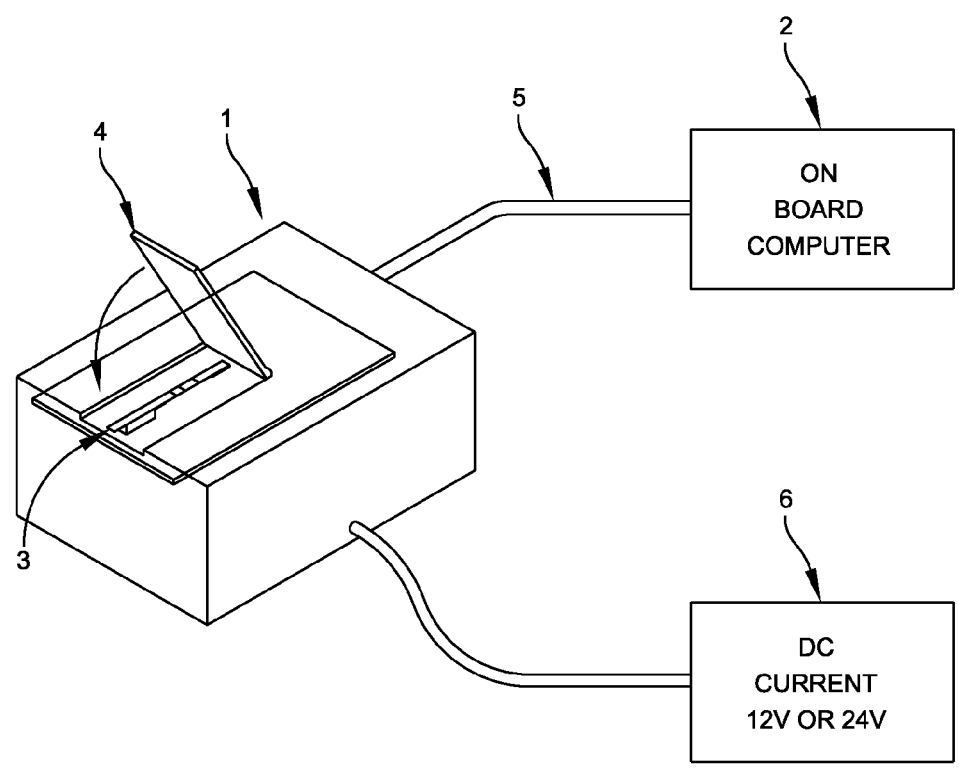
FIG. 1 shows a system in which an incubator and reader are combined in a single piece of equipment 1 which can be attached to an onboard truck computer 2 and onboard power source 6.

It is beneficial to provide a mechanism whereby central facilities can receive information concerning agricultural products, such as milk, prior to arrival at the central storage facility and/or processing facility. Such information can include results from a diagnostic test such as a test strip or film, for example a lateral flow test strip. Depending on the signal element of the test, equipment may be required to read and/or interpret the test result. In one example, a test strip is configured to provide a color change on the test strip that can be detected by sensing a decrease in light reflectance from a strip. The results can be detected by an optical sensor that is positioned to detect light reflected from the test strip. In another example the optical sensor is positioned to detect transmission through a test strip. In another example, a test provides a luminescent result and the result is detected by a luminometer.

Regardless of the type of equipment used, microprocessing capabilities are required including for result detection and analysis. In addition, a power source may be required. To send the result to the central facility, a data transmission capability is required. In many cases, onboard vehicle computers and other onboard systems or other systems readily available to truckers and other vehicle operators, provide some or all of those requirements.

Onboard computers are prevalent in motor vehicles. Such computers typically perform a variety of tasks including data sensing, data interpretation and data retention. Onboard computers can either be built in to the motor vehicle or a separate system carried within the motor vehicle such as a laptop computer or hand-held communication devices with appropriate microprocessing capability and the like. Also, either within the onboard computer system, or in a separate onboard system, the vehicle will often have data transmission capabilities for example through mobile communication devices such as mobile phones, satellite phones and other forms of both wireless and wired communication and data transmission tools.

By utilizing the onboard systems, analytical equipment such as optical sensors can be provided at minimum cost to the hauler, processor, farmer and other users. For example, a "stripped down" package can be provided that excludes either or both a battery or a microprocessor or has only a backup battery option or limited microprocessing capability. Such low-cost testing equipment is particularly important in transit testing, for example transit testing of milk, which is extremely price sensitive. The extra cost of redundant power supplies, microprocessors, LCD's, and keypads can, thereby, be eliminated. Other testing components can also be included, for example an incubator, which also utilizes the onboard power and may also utilize an onboard microprocessor. Making the equipment cleanable, particularly when sensitive detection sensors, such as optical sensors, are used, can add to the reliability and ruggedness of the equipment. Such reliability and ruggedness is particularly important in the non-laboratory environment including the transit testing environment.

Combining a reader and incubator into a single system that allows concurrent incubating and reading of a test, such as a test in a lateral flow test strip format, has further advantages. Such a combination can simplify test operation, improve test reliability, improve speed to result, reduce the possibility of mistakes, reduce the possibility of interference from debris and reduce the options for trickery by limiting operator (human) interaction and/or dynamically assessing test strip development during testing. Such dynamic assessment can be either by an onboard microprocessor that receives test data from the reader-incubator or by microprocessing components incorporated into the reader-incubator.

Aspects also can include a color sensor component. Such color sensor component can be configured as a separate sensing component within a reader-incubator or, depending on the reader used to read the test strip result, a singular component that detects both development on the test strip and color coding. Test strips, and other diagnostic tests, can be coded with a color that defines the test being run. For example, a red color might indicate a test to be used to detect beta-lactam antibiotics. Various matrices can also be delineated by the color system. In the red example, after the reader-incubator detects the red color on the test strip, the reader-incubator can be automatically configured for that specific test, for example by temperature adjustment of the incubator and selection of appropriate result parameters within the reader-incubator. Such color sensor can alternatively or also be configured to utilize onboard microprocessing capability. Such a reader-incubator can also be configured to utilize microprocessing components within the reader-incubator.

Aspects of an integrated diagnostic test reader-incubator include configuring the reader-incubator to both receive electrical current from a power source and to incubate a diagnostic test. The reader-incubator can also be capable of both reading a diagnostic test and sending a data transmission to a microprocessor onboard a motor vehicle. The data transmitted can be used by a microprocessor to determine a test result. The data transmitted can also be used to determine other information concerning the test strip such as areas of reduced reflectance caused by dirt/debris and information concerning whether the testing procedure was properly performed. Aspects include programming the onboard microprocessor to receive the data transmission from the diagnostic test reader, such as an optical reader. For testing, the agricultural product is contacted with a diagnostic test and the diagnostic test is incubated by the reader-incubator until a change occurs on the diagnostic test, the change representing the test result, and wherein the data corresponding to that change is detected by the reader and transmitted to the microprocessor. The microprocessor capability can either reside substantially or completely in the onboard vehicle microprocessor. Some or all microprocessor capabilities can also reside within the reader-incubator. Similarly, the reader-incubator can rely partially or completely on a motor vehicle power or include an integral battery.

In some aspects a communication is established between the reader-incubator and a wireless transmission device so that the wireless transmission device can transmit test results to a remote location.

Aspects also include a removable optical window between the diagnostic test and a sensor portion of a reader-incubator. The optical window can be cleanable and replaceable and can be composed of clear polyvinyl chloride plastic. The optical window can also be composed of glass.

A diagnostic test can be a lateral flow test strip in which a result is detected by the binding of a detectable analyte within one or more areas on the test strip. The lateral flow test strip can be read in a reader-incubator configured to include a housing, the housing having both a hood and a cavity, the cavity configured to receive the lateral flow test strip, the hood configured to enclose the cavity.

A test strip can be positioned relative to a sensor within the reader-incubator so that a change on the test strip can be detected by the sensor, the change resulting from a light source positioned to impact the test strip so that changes on the test strip, such as colorimetric changes, indicated by reflectance changes on a test strip, can be detected and measured.

DETAILED DESCRIPTION

We describe herein various embodiments in which onboard vehicle systems can be used in conjunction with diagnostic equipment such as optical sensors/readers and incubators. The onboard systems can be used for any or all of microprocessing, power and data transmission. Specialized software programs can be loaded onto the onboard computer and can provide instructions on reading and instructions on interpreting the data from a diagnostic test. Some embodiments also include using microprocessing capabilities that can be incorporated into the reader-incubator for some or all of the required microprocessing requirements. Other embodiments include utilizing power sources either or both from a battery within the reader-incubator and a motor vehicle power source.

One category of diagnostic test that can be run utilizing an onboard system is a lateral flow test strip for the detection of unwanted residues, such as antibiotics and/or toxins in an agricultural product such as milk, grains and other such agricultural products and foods. Such test strips can include elements that provide a signal, such as a reflectance change, that can be detected by equipment such as an optical reader. Diagnostic test strips are used for a variety of detection applications in a variety of matrices such as blood, urine and food such as milk.

Some lateral flow assays are membrane-based test devices in which a sample that is suspected of containing an analyte of interest is placed at or near one end of the membrane strip. The sample can be carried to the opposite end of the membrane strip by a mobile phase that traverses the membrane strip and encounters one or more reagents. The reagents can include binders for the analyte. Binders can be mobile and, therefore, flow with the sample or be immobilized on the test strip as a capture agent. Depending on the assay configuration, either the analyte binder, the analyte itself, or some other reagent in the assay system, will be captured by the immobilized capture agent and, thereby, produce a detectable signal. The signal can be generated by a label provided within the assay. The detectable signal can be measured, such as by an optical reader. The data can then be either sent to an onboard microprocessor for analysis or analyzed using microprocessor capabilities within the reader. Alternatively, some data can be interpreted by an onboard microprocessor and some by a microprocessor capability within a reader-incubator.

The presence and, in some cases, the concentration, of an analyte on a reagent strip sample may be determined by measuring the light reflectance from an area of color development on the strip. For example, percent reflectance can be used to determine the result. Optical transmission can also be employed in some embodiments.

Readers can include a light source and a detector aligned such that the light from the light source shines onto the test strip containing the sample and is then reflected onto the detector, such as an optical detector. The light source can include an incandescent bulb, a fluorescent tube, a light emitting diode or the like. An example of such an optical reader is described in U.S. Pat. No. 6,124,585 (Apparatus for measuring the reflectance of strips having non-uniform color), issued Sep. 26, 2000, and incorporated herein by reference. In addition, a variety of types of readers may be employed depending on the type of test and signal emitted including spectrophotometers, LCD cameras, reflectance readers, luminometers, fluorometers, bar code image capturing, CMOS cameras, scintillation counter, magnetic detectors and other instruments.

When the diagnostic test, such as a test strip, requires optical sensing, various optical sensors may be useful including a single photodiode, multiple photodiodes, a linear photodiode array, a charged couple device and a complimentary metal oxide semiconductor including those sensors described in U.S. patent application Ser. No. 12/678,388, filed Aug. 18, 2010, and incorporated by reference herein. The optical sensor and light source can be positioned above or below the test strip. When the sensor is, for example, above the test strip, a removable optically clear window can also be positioned above the test strip. When the sensor is below the test strip, the removable window will also be positioned below the test strip. The removable windows can be replaceable and they can also be cleanable. Such removable optical windows can be particularly useful in the non-laboratory environment in which transit testing occurs. Such an environment may require testing equipment be especially rugged.

In one embodiment an optical reader-incubator is used to measure the reflectance from a test strip. The housing can have an exterior and interior and contain an opening for insertion of test strips. Alternatively, a hood-like device can be used so that a test strip is placed inside a hood and the hood closed for reading and/or incubating. A series of discrete electrical light sources, for example a plurality of light emitting diodes (LEDs), can be mounted on a printed circuit board, for example on the top surface of the printed circuit board, located within the housing. An LED can be configured and current driven to emit an illumination pattern suitable for reflecting from the test strip located directly above an LED. Light from the LEDs can be reflected off the test strip and through an aperture in the circuit board. The light reflected through the circuit board can be directed to an optical detector within the reader-incubator. For example a first mirror mounted under the circuit board can direct the light through a focusing lens to a second mirror. The second mirror can direct the focused light onto an optical detector mounted beneath the circuit board. A reader-incubator can output a data stream that can be converted by an on onboard microprocessing unit into a series of 128 distinct one-dimensional numeric readings. The 128 readings can be taken multiple separate times and averaged. The data can also, alternatively, be analyzed by a microprocessor unit within a reader-incubator or by an onboard microprocessor.

In another embodiment, in which a charged coupled device (CCD) or complementary metal oxide semiconductor (CMOS) is used as an image sensor, a reader can be programmed to analyze a test strip through two-dimensional readings, rather than through the one dimensional, 1×128, readings. In examples, a 5×128 or 512×492 matrix of "pixels". Such a 2-dimensional reading widens the reflectance capture area to capture reflectance directly from the sides of a test strip.

An optical reader-incubator may include a plurality of LED's or, alternatively, one LED is used with an optional feedback loop. The feedback loop can use a photodiode to sense light output variation from the single LED. If light output changes a signal is sent so that an appropriate adjustment can be made, for example, an increase or decrease in current to the LED. Light output from the LED may be reflected either directly off the test strip or, alternatively, directed to a first mirror for reflection to, and then off of the test strip to a second mirror. The second mirror directs the light through a lens to an imager, for example a CCD or CMOS imager.

A reader-incubator can utilize power provided by a USB port from an onboard computer. For some applications, particularly applications requiring current levels not available from a USB port, separate power connectivity may be required, for example using the cigarette lighter, along with the RS 232 port for data transmission. A battery can also be included within the reader for a separate, independent power supply.

In an embodiment a test strip containing a sample is placed inside the reader and is both incubated and read without additional manipulation. In such an embodiment, incubator temperature can be controlled to maintain a temperature sufficient for test strip incubation and to prevent overheating. Optic components can be chosen for use at increased temperatures (above room temperature). Insulation can be useful to protect temperature sensitive optical sensor components from elevated temperatures. Thermoelectric cooling utilizing the "Peltier effect" in a "Peltier" device can be used to prevent overheating. Embodiments include using aluminum blocks in the incubator.

In an embodiment the housing of the reader-incubator has an exterior and interior and contains a hood-like mechanism that is opened for insertion of a test strip. The hood can be lifted and the test strip inserted into a heating cavity such as a metallic, for example aluminum, cavity designed to receive the test strip. The cavity can be surrounded by insulating material such as a plastic material, for example a thermoplastic such as polyoxymethylene, known as Delrin (DELRIN is a registered trademark of DuPont) that insulates the cavity and does not deform when heated to the temperatures required for testing. Connected to the cavity can be electronics to heat the cavity to a preset temperature. A ceramic heater or resistive element heater are examples of useful heaters. The cavity can be designed to be small to draw minimum current. Heating only essential areas and providing insulation around those areas minimizes power requirements. Use of various heating algorithms can be useful. For example, a proportional integrated derivative (PID) can be used. Such algorithms are particularly useful when test results are affected by small temperature variation. Embodiments include incubator control systems that eliminate the need for manual adjustment by use of embedded, digital temperature sensors and digital potentiometer that provides both accurate temperature reporting and a mechanism by which a micro-controller can adjust a stand-alone, analog, incubator control circuit. Power can be supplied either by a motor vehicle or internal battery.

In certain embodiments cooling might be necessary, for example to stabilize the environment of either or both a test medium and sample prior to incubation.

One problem with running a diagnostic test on a truck is the increased risk of contaminating system optics with dirt and debris. For example, when milk is tested, dried milk can be accidentally introduced into a reader such as, if an optical reader, in the optical path used for result detection. If system optics are above A test strip, as described in certain embodiments herein, the problem is reduced by the force of gravity pulling debris and dirt away from the optics. The problem, however, is not eliminated. The problem is exacerbated in embodiments in which optics are below a test strip. Such can be the case when a system includes incubator and reader in a single device for transit testing. When using an optical reader-incubator, between the test strip and the sensor portion of the reader can be a clear, optical window. The optical window can block debris from the test strip from contaminating the sensor itself or other system parts used with the sensor such as lenses and mirrors. The clear optical window can be removable and cleanable or can be removable and disposable. The removable/cleanable window can be the only window used or be in addition to a fixed window covering other portions of the optics. In one embodiment, the window material includes clear polyvinyl chloride (PVC) plastic. The window can be mounted on a slide and inserted into the reader device between the test strip area and the sensor. The light source can be positioned in variety of ways and in a variety of configurations relative to the optics. Some embodiments of removable and cleanable optically windows are described in WO2009038798A1: Assay Reader Insert and Method of Maintaining a Reader, filed Sep. 22, 2008, hereby incorporated by reference. Other configurations are also possible in which system optics are protected by one or more optical windows.

Embodiments also can include using either an onboard microprocessor or a microprocessor capability within the reader-incubator to both monitor test progress, such as test progress on a lateral flow test strip, and determine a test result from the lateral flow test strip. When an onboard microprocessor is used, data can be transmitted to the microprocessor for interpretation. Such data can include not only data relating to the test result but also data relative to test progress on the test strip. For example, the reader-incubator can be activated by closing the hood that encloses the cavity. Prior to determining the test result the microprocessor, whether within the reader or onboard the motor vehicle, receives from the reader data relative to test progress on the test strip. For example, prior to determining the test result, the reader can be configured to transmit data to the microprocessor that can be used to sense whether an adequate flow of a reagent occurred on the test strip while the test strip was within the cavity and/or whether one or more lines were present on the test strip prior to contact of the strip with the sample to be tested. Prior to determining the test result the reader can similarly be used to receive data that can be used to determine whether debris has contaminated the sensor. For example, if debris is present on a lens or within an optical light path, then the data received by the reader will show a reduction in reflectance on the test strip. Such reduction in reflectance, prior to sample flow on the strip, can be the result of debris and thus the sensor requires cleaning and/or recalibration.

If a test strip is valid, for example does not have areas of reduction in reflectance prior to sample flow, then the test can proceed. The test result can be determined by a comparison between at least two lines on the test strip, for example by a comparison of changes in reflectance values of two lines on the test strip. By combining the reader and the incubator, speed to result can be enhanced, for example to as little as less than 60 seconds or even less than 30 seconds.

To determine that a test has run properly, predetermined optical measurements, such as reflectance values, can be stored electronically either within a microprocessor component of the reader or within an onboard microprocessor. The preset values, or preset parameters, can include a theoretical reflectance value from a one or more test lines and/or one more control lines on the test strip and can also include a difference between the theoretical reflectance value for the one or more control lines and the theoretical value for the one or more test lines. A preset parameter can also include a value for the test strip after receiving the reagent flow thereon.

Reader-incubators can include optical sensors such as a single photodiode, multiple photodiodes, a linear photodiode array, a charged couple device and a complementary metal oxide semiconductor in a variety of formats.

While closing of the hood, or some other trigger can be used to begin test operation, some reader-incubator combinations may be capable of a variety of testing sequences. For example, different analytes and different matrices require different temperatures of incubation. Similarly, different matrices and different analytes have different associated standard curves and different positive and negative cutoffs (control points). Some readers are programmed with multiple channels, each of which has separate parameters associated with the related test. Embodiments include an automatic channel selection initiated by a coding on a test strip, such as a color coding, and read by the reader-incubator either by a separate optical reading system or the same system that read the test result. That is, a test strip can include a color coding portion that, after test initiation, will be read by a color reader to determine either or both a reader channel and the appropriate incubator temperature. For example, a photodiode with a wide dynamic range of sensitivity to red, green and blue wavelengths can be used as the detector. Red, green and blue LEDs can be used as the light source. Each LED can be turned on sequentially and the detector used to determine the reflectance of each of the colors. A black surface (totally absorbent as containing no color) will produce little or no reflectance of the given LEDs wavelength and, therefore, the detector will produce low output readings. A white surface will produce maximum reflectance of all three LEDs. Various colors (depending on its content in the surface measured) will produce output from the detector at varying levels.

The LED light source for the color sensor can be a red, green, blue LED device in a single package. The LED light source for the color sensor can also be three discrete LEDs. Similarly, a single white LED and three discrete photodiodes, with narrow bandwidth responses at the red, green and blue wavelengths can be used as a detector front-end.

Rather than, or in conjunction with, color coding and a color sensor Some embodiments can also employ technology such as Radio Frequency Identification (RFID) technology, bar code technology biometrics, magnetic strips, optical character recognition, smart cards and voice recognition. Such technology can enable a variety of tracking and control issues to be addressed in the context of diagnostic tests including food sanitation tests. Such technology can also utilize onboard systems for power and micro processing capabilities.

Various triggers can initiate test strip analysis either by a microprocessor within the reader-incubator or by a microprocessor onboard a motor vehicle (after test data is transmitted to it from the reader-incubator). For example, a hood closing can initiate test operation, including optical measurement. Alternatively a separate switch can be used to initiate test operation after the hood is closed. In either case, a first reading can determine whether a proper test strip is in place. If a test strip is detected a reading sequence is begun. For example, optical measurement, such as to detect light reflected off the test strip, can utilize values, such as average reflectance values, in certain areas of the test strip. Initially the system can analyze the test strip to determine if the optical path is clear of interference, such as from debris. Debris can be in any number of locations in the optical path including on a test strip or test strip container. Concurrently with analyzing the optical path for debris, or subsequent thereto, the system can analyze a test strip to determine if line development has already occurred. That is, whether a proper strip has been inserted into the cavity. Test strips configured to develop within certain areas, such as a test line and control line, should have no initial development in those areas. For example, lines configured to develop a change in reflectance when contacted by reagents and sample should not develop until flow of sample and reagents has arrived and binding has occurred. Such flow will not have arrived at the time of an initial, for example 3 second, read. As such, if line development is detected at the initial test strip analysis then an error message will be delivered to the user and further readings, for example further optical measurements, can be aborted. This mechanism can detect the use of pre-run (known negative) test strips or pre-marked strips. Generally, when reflectance is reduced on an unused test strip, either by the presence of line development or other darkening of the test strip away from baseline, such as by debris contamination, the reduction in reflectance can inform the user that something has occurred either on a test strip or in an optical path so that a result should not be accepted.

After initial optical readings are found satisfactory and appropriate reader parameters and incubator temperatures are selected, either manually or automatically, further optical readings, for example approximately 15 seconds after sample has been applied, can be used to determine whether adequate flow has occurred. For example, optical readings can determine whether or not reagents have flowed between a sample application region and a downstream line such as a test line. The presence of label, such as colored particles, for example gold sol beads, flowing in the mobile phase, and the resulting reflectance changes on the strip between the sample application area and a first test line, can inform the user that flow is occurring and return an error message if no flow is detected. A test strip lacking predictable reflectance changes might either have had no sample flow, or inadequate sample flow. Certain measurements can also indicate whether excessive flow has occurred, as in the case where too great a volume of sample has been applied to a test strip and possible reflectance change due to reagents is overwhelmed by the excessive sample volume. Reflectance changes between the sample application area and result detection areas, such as test line and control line, can be temporary and disappear as the mobile phase flows. If optical measurements are taken such temporary/non-permanent changes can be detected.

If a test strip, or other assay type, has passed the preliminary readings, readings can begin to determine a result. For example, after approximately 30 seconds test line and control line analysis can begin. When there is enough differentiation between the test and control, a result can be provided. Typically, negative results and more extreme results can be provided sooner and results closer to threshold levels will require longer time. For example, in the case of a test in which the reflectance value on a test line relates inversely to an amount of analyte, if the test line reflectance is reduced to a certain level then a negative result can be called.

EXAMPLE 1

FIG. 1 illustrates an embodiment in which a reader-incubator 1 has, as its power source, a motor vehicle and as its "brains" an onboard computer (microprocessor) system 2. The diagnostic test is placed in cavity 3 and covered over by a door-like device 4. Programming code, such as code written in a standard language such as C or C++ can be loaded to the onboard computer 2 for interpretation of data output from the reader. In addition, the onboard computer 2 can provide data management, memory and control functions that are required by either the reader or the incubator. Test results can be transmitted through the motor vehicle systems to a remote location to assist with logistical control. The power source can be through a USB connection 5 to the onboard computer 2 or through separate power connectivity 6, for example to the cigarette lighter power source. The incubator can be well-insulated to minimize power requirements and temperature variations. Temperature ranges up to 65 degrees C. may be required for certain diagnostic tests. The reader can be a variety of types of readers capable of utilizing onboard microprocessor and power.

Figure 2:
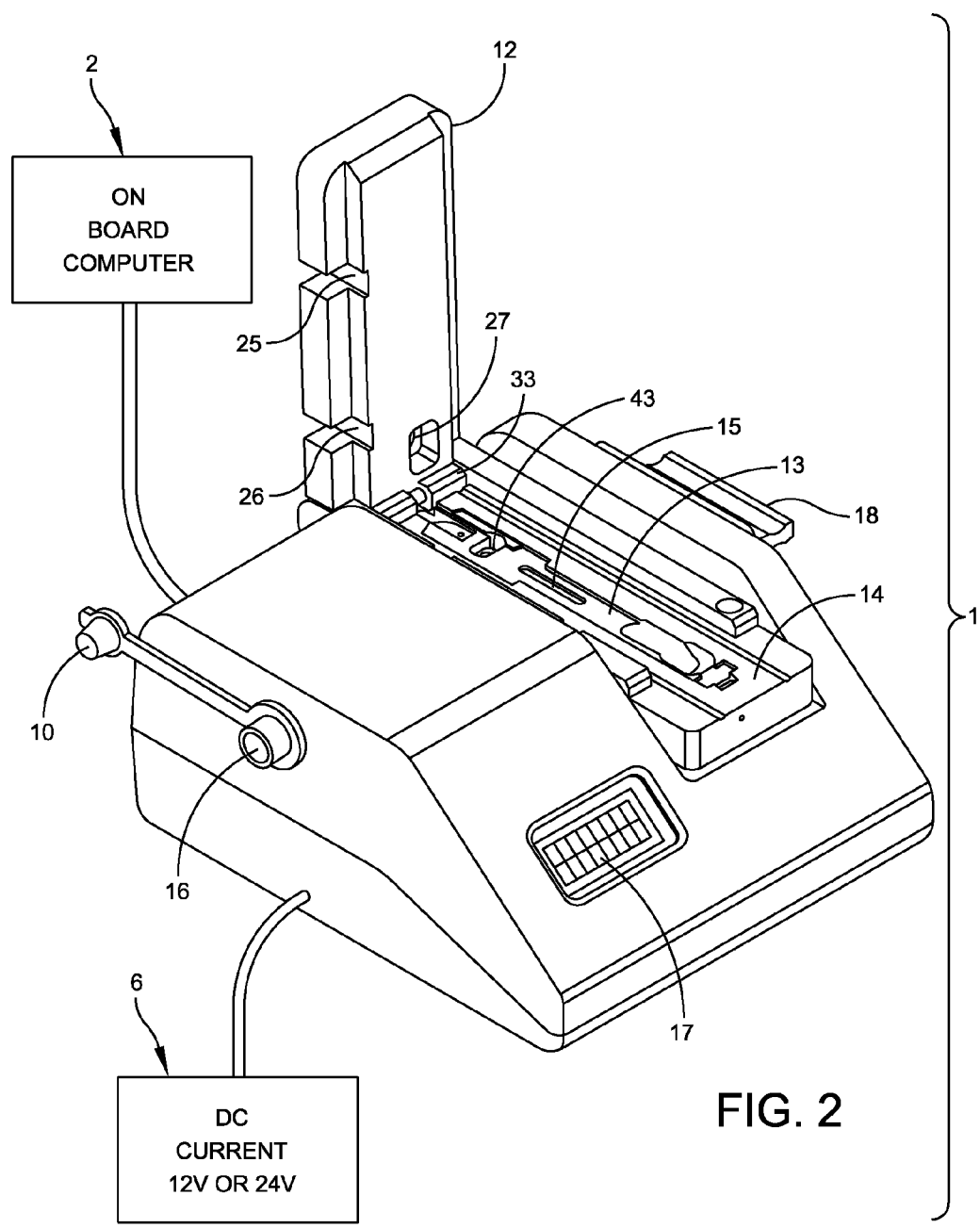
FIG. 2 is an isometric view showing an embodiment of the FIG. 1 system with a combined reader-incubator with hood 12 open showing cavity 13 in base 14.
Figure 3:
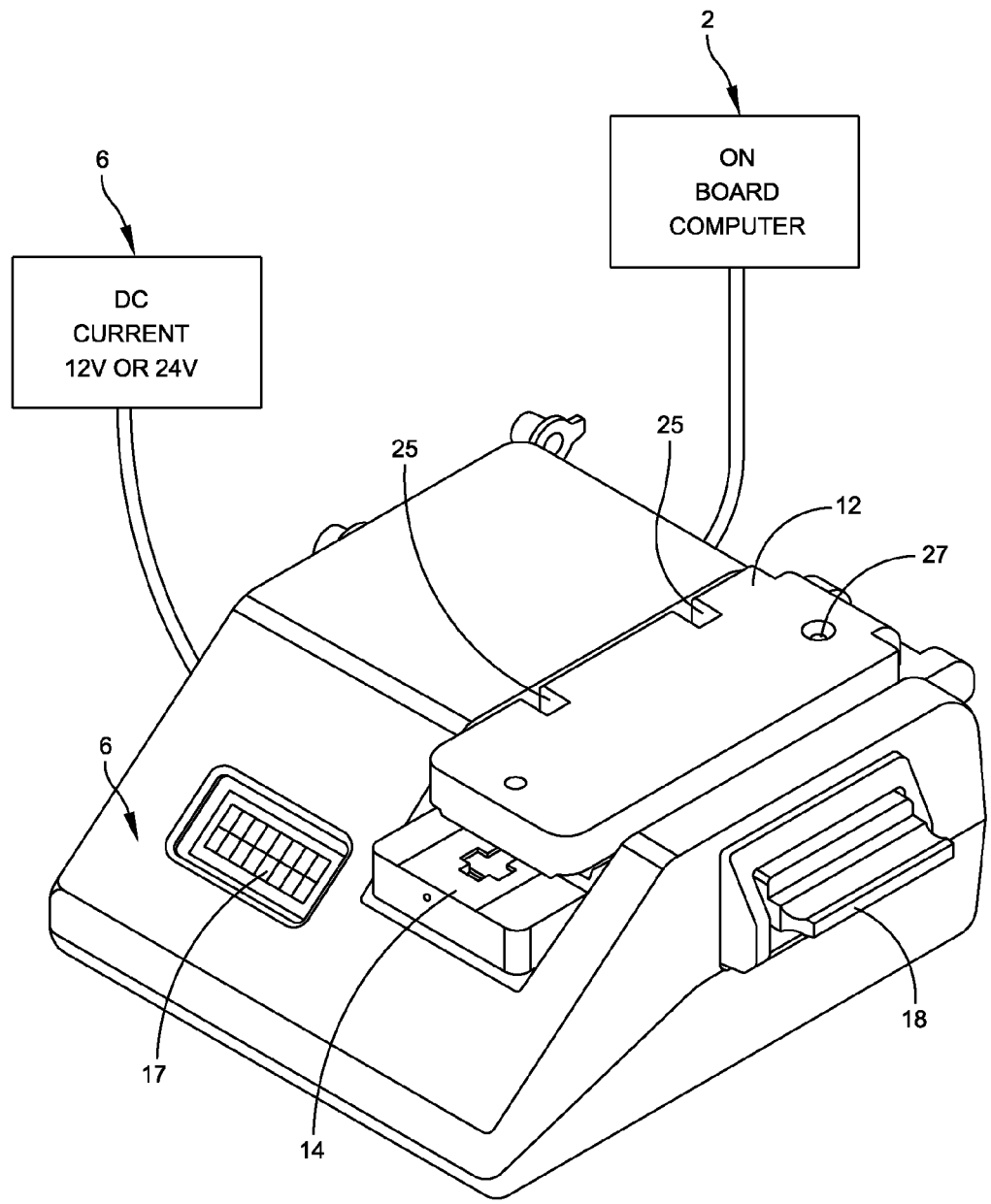
FIG. 3 is an isometric view showing combined reader-incubator 11 with hood 12 closed.
Figure 4:
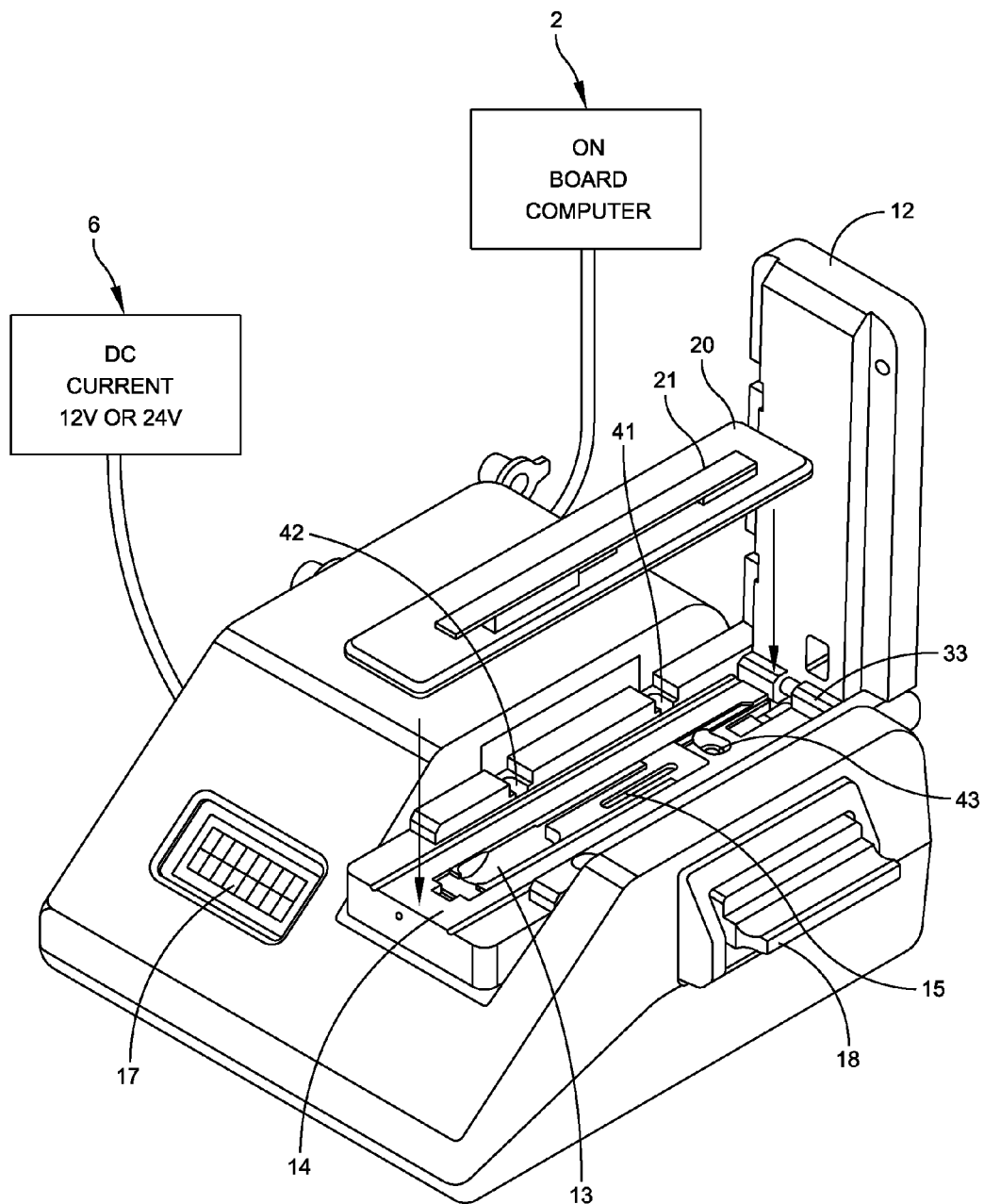
FIG. 4 is an isometric view showing test strip 21 and test strip enclosure 20 with hood 12 open and cavity 13 configured to receive test strip 21 and enclosure 20.

FIGS. 2 and 3 show an embodiment of reader-incubator 1. In FIG. 2 hood 12 is open and in FIG. 3 hood 12 is closed. When open hood 12 exposes cavity 13 in insulated base 14. Hood 12 can be composed of a variety of materials, such as insulating materials, including plastic. Hood 12 can be configured to close over cavity 13 when test strip 21 (not shown in FIGS. 1, 2 and 3), within test strip enclosure 20 (not shown in FIGS. 1, 2 and 3) is placed therein. Closing of hood 12 can initiate the optical reading of test strip. Closing of hood 12 can also initiate incubation. Alternatively, cavity 13 can be heated prior to receiving test strip 21. Cavity 13 includes aperture 15 through which light can illuminate test strip 21 and through which changes on test strip 21 can be detected by optical sensor, positioned below cavity 13, and reported to the user through optional result display 17. Removable optical window can be positioned between optical sensor and cavity 13 and attached to handle 18 for ease of removal. Opening 16 with cover 10 can provide an inlet for compressed air. Optical window can be removable by pulling handle 18. Cavity 13 can be composed of heatable material and protected and insulated by base 14 and hood 12, when closed. Openings 25 and 26 in hood 12 allow access to adjustment screws 41, 42 when hood 12 is closed. Adjustment screws can also be accessed when hood 12 is open. Adjustment screws 41, 42 and 13 can be used to properly position cavity 13 in relation to optics so that changes on test strip 21 can be fully detected. FIG. 3 shows adjustment screw 43 in cavity 13 and adjustment screws 41 and 42 in insulated base 14. Hinge 33 allows easy opening of hood 12. Box 2 depicts 12 volt or 24 volt current connection to the reader-incubator. Box 6 depicts an onboard microprocessor connected to the reader-incubator. As shown in FIG. 4, test strip 21 in enclosure 22 is placed into cavity 13 for incubation and reading through aperture 15.

Figure 5:
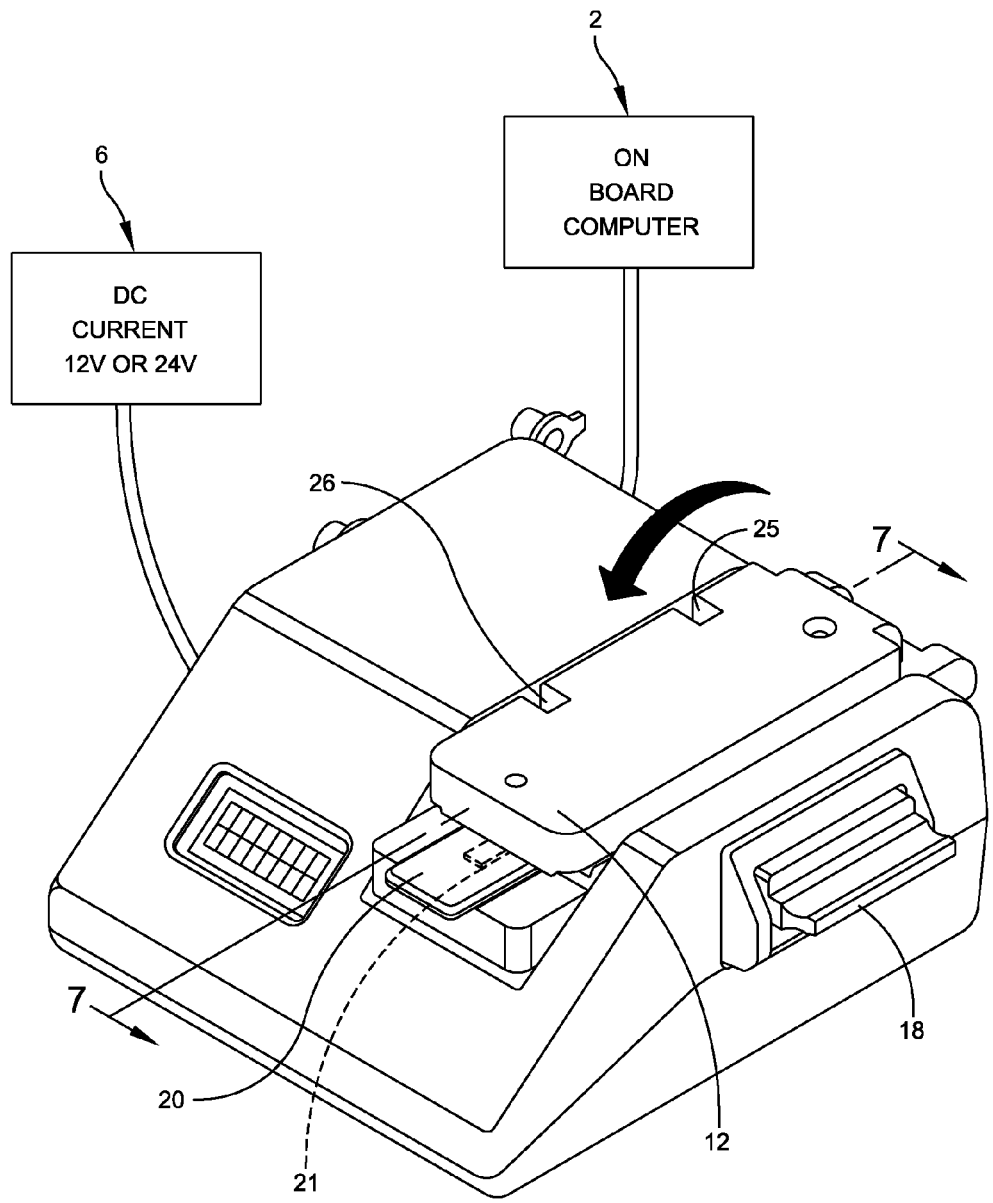
FIG. 5 is a an isometric view showing test strip 21 and test strip enclosure 20 with hood 12 closed and test strip 21 and enclosure 20 protruding.

FIG. 5 shows hood 12 closed enclosing test strip 21 and test strip enclosure 22 that have been placed in cavity 13. When hood 12 is closed on test strip 21 within cavity 13 testing can occur including pre-result monitoring of test strip 21 for decreased areas of reflectance that may be caused by factors including debris within the optical path or an attempt by the user to fool the system by attempting to use pre-run, or pre-marked test strip.

Figure 6:
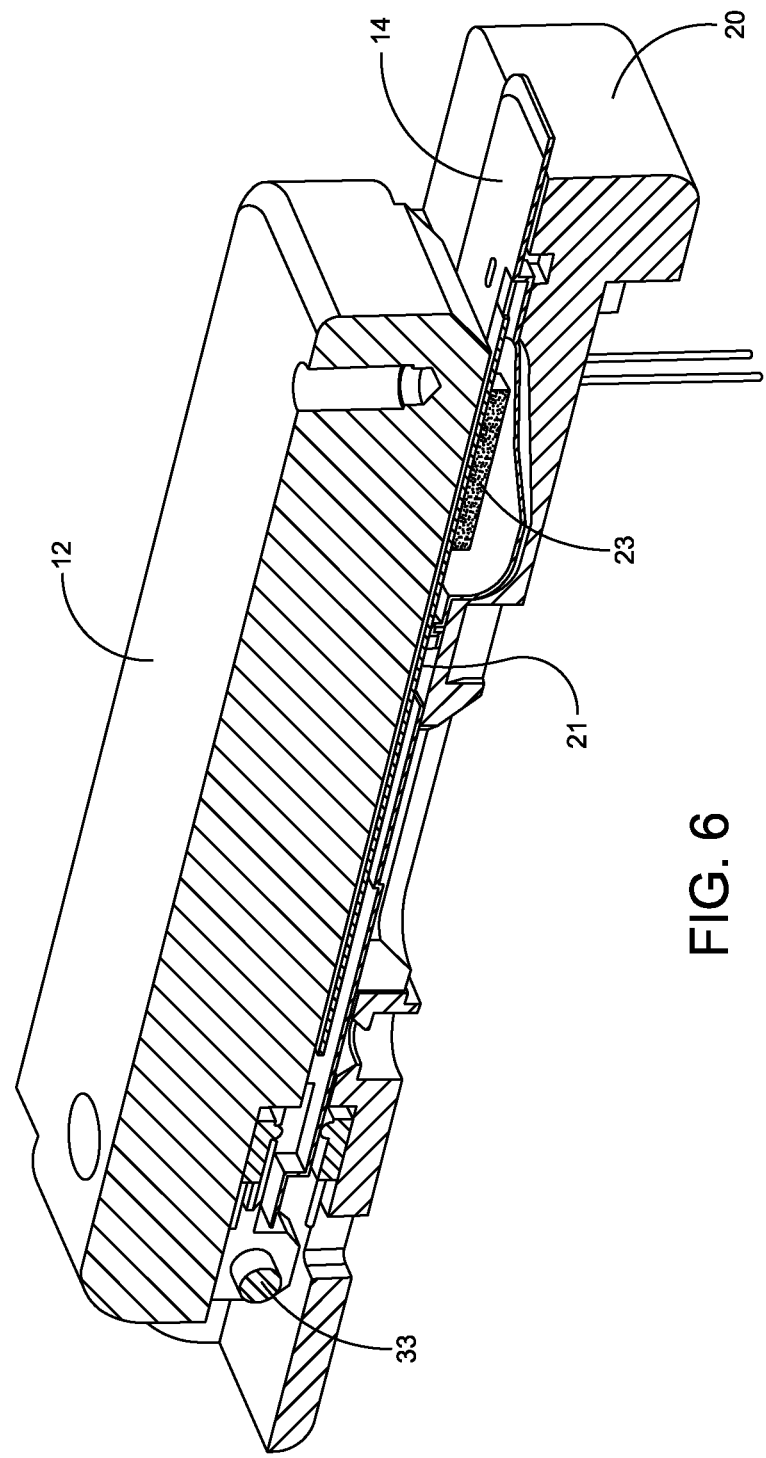
FIG. 6 is a partial cut-away cross-section of FIG. 5 showing test strip 21 within a cavity in closed hood 12.

FIG. 6 is a partial cross-section from FIG. 5 showing the hood 12 closed enclosing test strip 21 and test strip enclosure 22 that have been placed in cavity 13.

Figure 7:
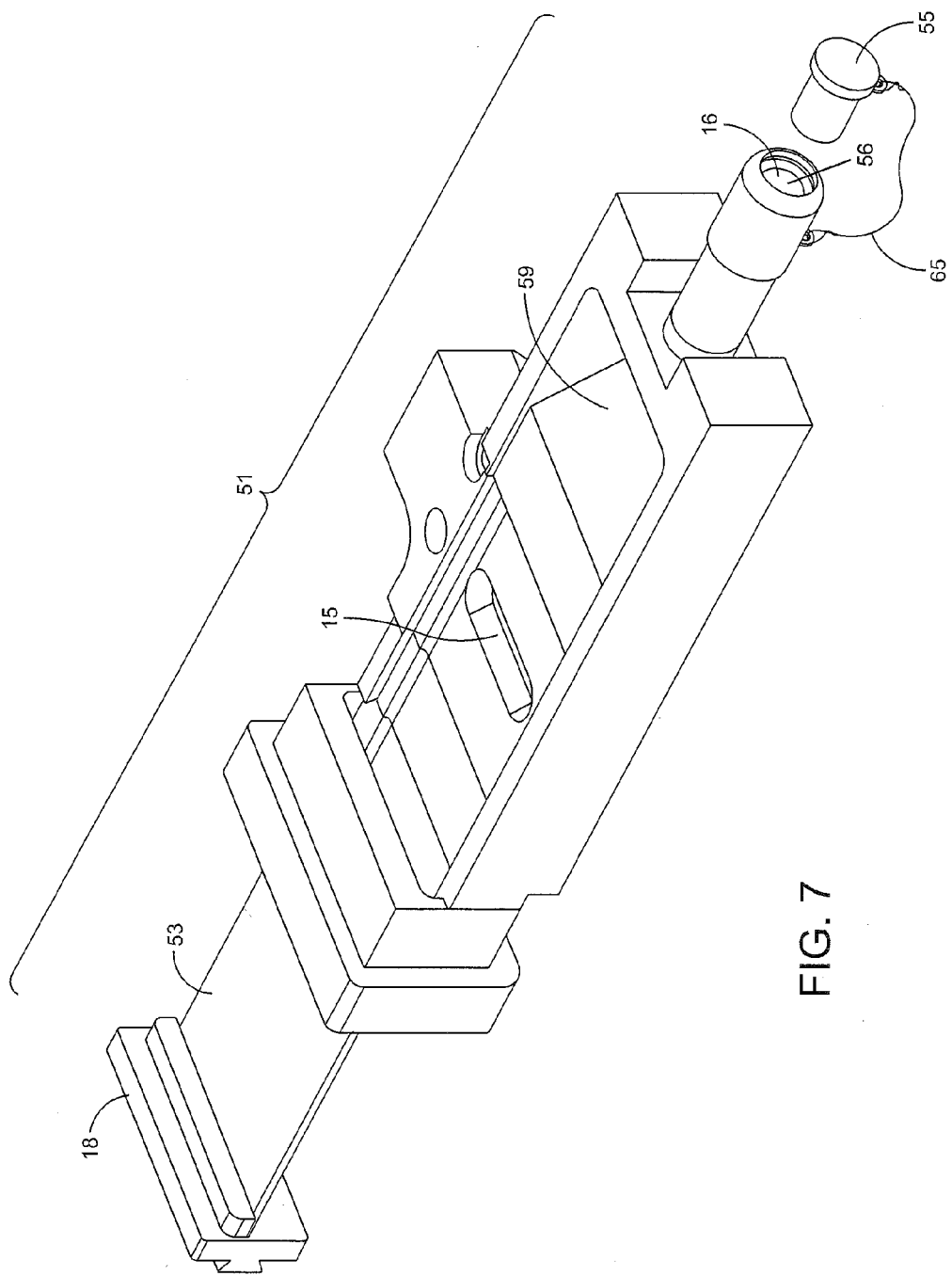
FIG. 7 is a partial perspective showing a module of an insert 51, including a removable window 53 where removable window 53 is partially withdrawn from insert 51 and air inlet cap 55 is removed.
Figure 8:
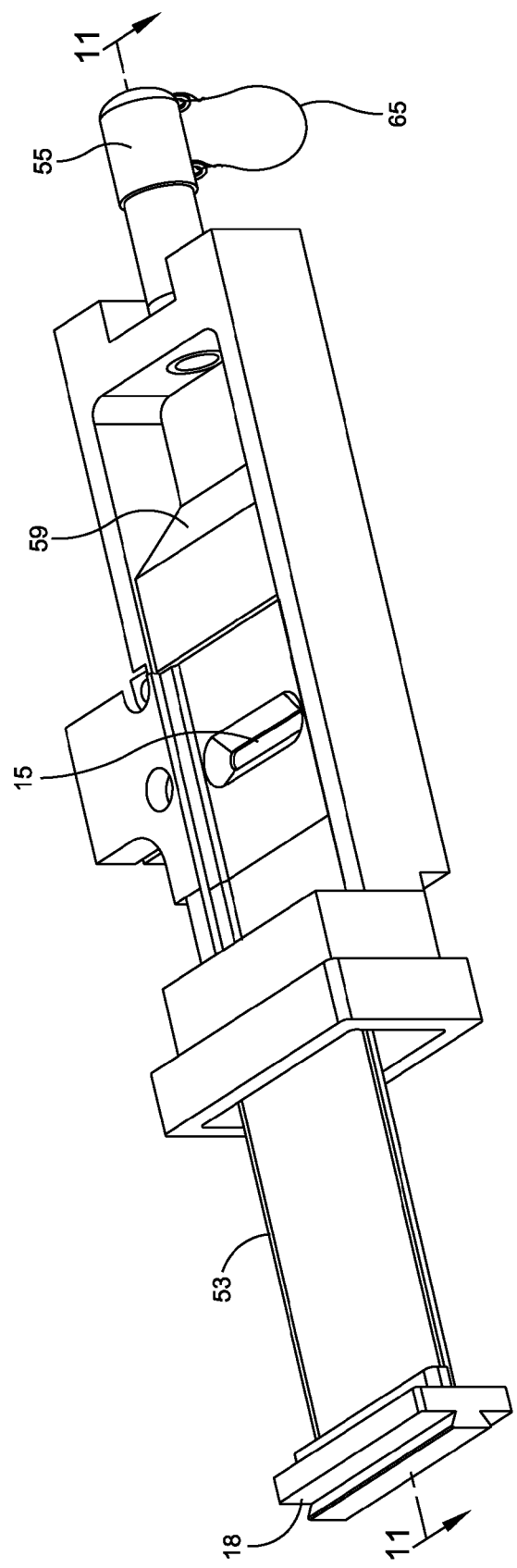
FIG. 8 is a partial perspective showing a module of insert 51, where removable window 53 is partially withdrawn from insert 51 and the air inlet cap 55 is affixed to an air inlet.
Figure 9:
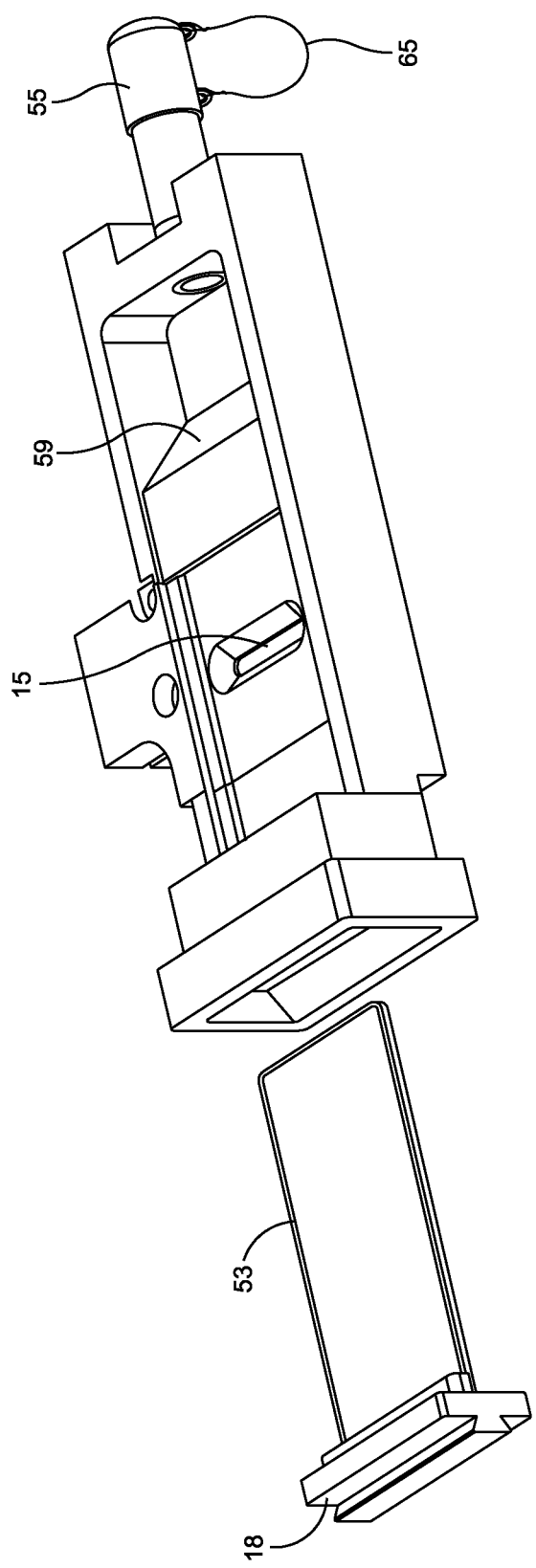
FIG. 9 is a partial perspective showing a module of insert 51, where removable window 53 is withdrawn from insert 51.

FIGS. 7-9 show an insert module 51. These figures illustrate the removable optical window 53 in the withdrawn position, where the window 53 is removed from the cavity 15. The optical window 53 can be removed, for example, for cleaning and/or replacement, by pulling or engaging on the handle 18. In an optical reader, for example, a light source may then be used to illuminate the test strip 21 (not illustrated in these figures) through an aperture in a circuit board. In this embodiment, light may reflect off the test strip 21, which can then be focused onto an optical sensor positioned relative, for example, from above the aperture.

Figure 10:
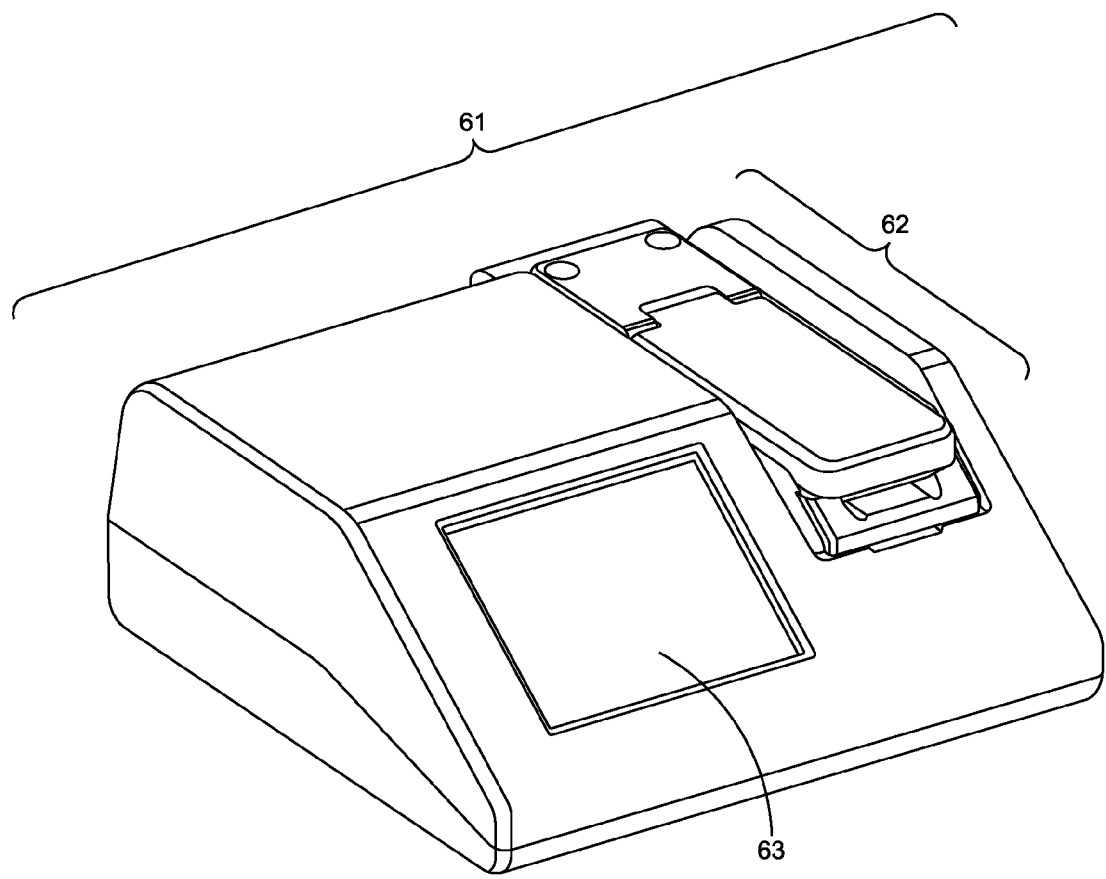
FIG. 10 is a perspective view of an embodiment of reader-incubator 11 with removable test strip incubation module 62.
Figure 11:
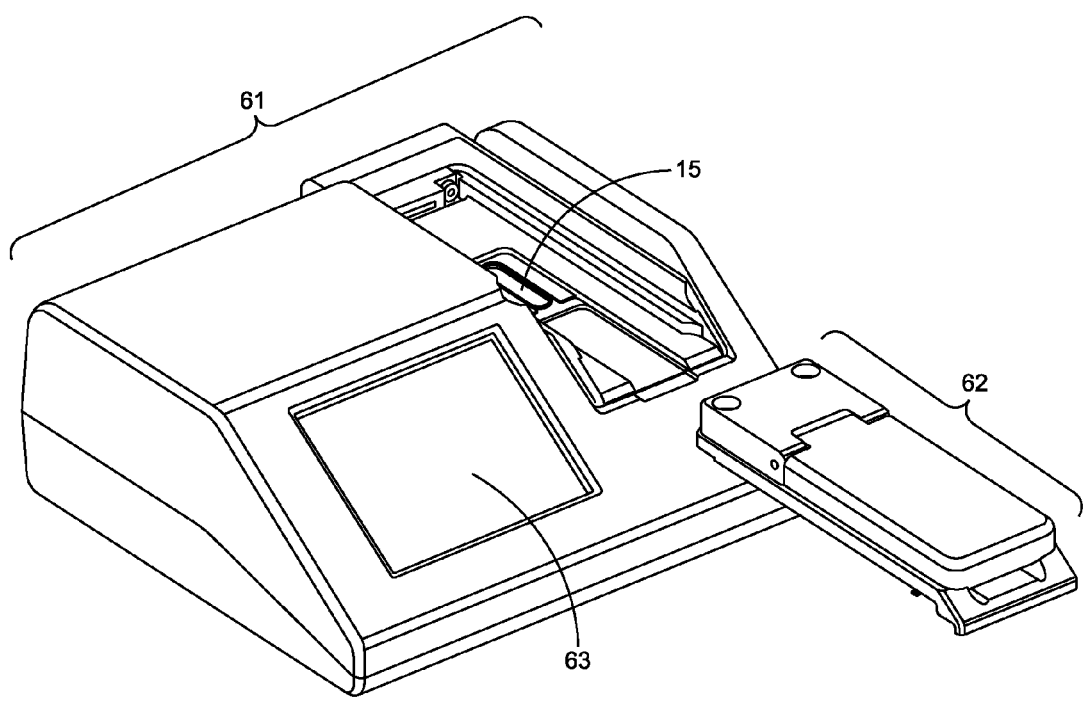
FIG. 11 is a partially exploded perspective view of reader-incubator 11 with removable test strip incubation module 62 removed from reader-incubator 11.
Figure 12:
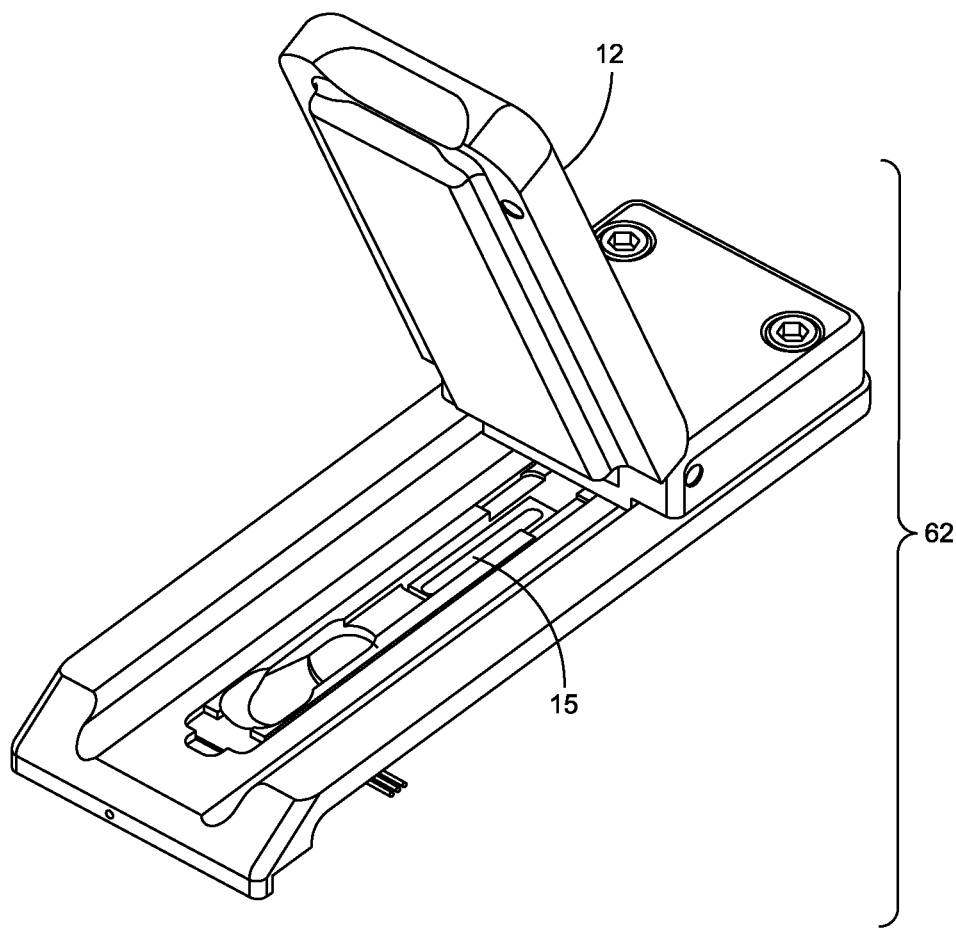
FIG. 12 is a perspective view of removable test strip incubation module 62 with hood 12 open.

FIGS. 10-12 show an embodiment of a reader-incubator, numbered here as 61. In this embodiment, test strip cavity 13 is part of a removable module 62. An optional touch-screen display 63 is included for ease of use. The removable module 62 can include one or more windows, such as optical windows, protecting system optics from contamination through aperture 15. An additional aperture can also be included (not shown) to align with the downstream end of test strip 21, such additional aperture can be aligned to be read by a color sensor, such as, for example, a photodiode with a wide dynamic range of sensitivity to red, green and blue wavelengths, within reader-incubator 61. Such color coding can be used to, after test initiation, be read by a color reader within the reader-incubator 61 to determine either or both a reader channel and the appropriate incubator temperature. Such a color coding aperture can also be protected by an optical window. Reader-incubator 61, like reader-incubator 1 can include connections for onboard microprocessor use and motor vehicle power supply.

The invention claimed is:

1. An apparatus to generate a diagnostic test result from an assay test strip, said apparatus comprising:
   a. an optical reader aligned in an optical path with said assay test strip, wherein said optical reader is adapted to acquire an image detection on said assay test strip;
   b. a microprocessor in communication with said optical reader, wherein said microprocessor is adapted to signal said optical reader to perform image detection of said assay test strip to generate said diagnostic test result; and
   c. a removable module having said assay test strip, an insulated base supporting a test strip cavity, and an optical window positionable between said test strip cavity and said optical reader, and wherein said test strip cavity comprises an optics aperture illuminating said test strip cavity and said removable module blocks debris from contact through said optics aperture to said optical reader in an assembled position, and detaches from said optical reader to expose said optics aperture in a removed position.

2. The apparatus of claim 1, wherein said assay test strip is a lateral flow test strip.

3. The apparatus of claim 2, wherein said removable module includes a repositionable hood to enclose said lateral flow strip.

4. The apparatus of claim 2, wherein said removable module includes at least one aperture adapted to align with a downstream end of said lateral flow test strip.

5. The apparatus of claim 2, wherein said removable module includes a cavity to receive said lateral flow test strip.

6. The apparatus of claim 1, wherein said microprocessor is onboard a motor vehicle.

7. The apparatus of claim 6, wherein said microprocessor interprets data transmission to determine said test result.

8. The apparatus of claim 6, wherein a power source is a power supply integrally associated with said motor vehicle.

9. In a lateral flow test strip assay system having a reader with an optical detector, an insert assembly comprising:
   a. a removable module positionable in said reader to align an assay test strip with said optical detector and having said assay test strip, an insulated base supporting a test strip cavity to receive said assay test strip, which is a lateral flow test strip, and wherein said test strip cavity comprises an optics aperture illuminating said test strip cavity and blocking debris from contact through said optics aperture in an assembled position; and
   b. a repositionable hood secured to said removable module to enclose said lateral flow test strip.

10. The apparatus of claim 9, wherein said insert assembly being removably positioned in-between said optical detector and said assay test strip.

11. The apparatus of claim 9, wherein said insert assembly being positionable in said reader to block debris from said optical detector.

12. The apparatus of claim 9, wherein said insert assembly is cleanable.

13. The apparatus of claim 9, wherein said insert assembly includes at least one aperture adapted to align with a downstream end of said lateral flow test strip.

14. The apparatus of claim 13, wherein said insert assembly includes a second aperture adapted to align with a coding reference on said lateral flow test strip.

15. An apparatus for testing a quality of an agricultural product to generate a diagnostic test result from an assay test strip, said apparatus comprising:
   a. an optical reader aligned in an optical path with said assay test strip, wherein said optical reader is adapted to acquire an image detection on said assay test strip;
   b. a microprocessor in communication with said optical reader, wherein said microprocessor is adapted to signal said optical reader to perform image detection of said assay test strip to generate said diagnostic test result; and
   c. a removable module positionable in said reader to block debris from said optical detector and having said assay test strip and comprising:
      i. an insulated base supporting a test strip cavity to receive said assay test strip,
      ii. an optical window positionable between said test strip cavity and said optical reader, and wherein said test strip cavity comprises an optics aperture illuminating said test strip cavity and blocking debris from contact through said optics aperture in an assembled position, and
      iii. a hood secured to said removable module to enclose said assay test strip.

16. The apparatus of claim 15, wherein said removable module being adapted to block debris from contact with said optical reader in an assembled position and detached from said optical reader in a removed position.

17. The apparatus of claim 15, wherein said microprocessor is onboard a motor vehicle.

18. The apparatus of claim 15, wherein said assay test strip is a lateral flow test strip.

19. The apparatus of claim 18, wherein said removable module includes at least one aperture adapted to align with a downstream end of said lateral flow test strip.

20. The apparatus of claim 15, wherein said removable module is slide-mounted in said optical reader.

* * * * *